(12) United States Patent
Seto et al.

(10) Patent No.: US 8,425,544 B2
(45) Date of Patent: Apr. 23, 2013

(54) FLUID INJECTION DEVICE

(75) Inventors: Takeshi Seto, Chofu (JP); Kazuyoshi Takayama, Sendai (JP); Atsuhiro Nakagawa, Sendai (JP); Viren Ivor Menezes, Karnataka (IN)

(73) Assignee: Seiko Epson Corporation, Tokyo (JP)

( * ) Notice: Subject to any disclaimer, the term of this patent is extended or adjusted under 35 U.S.C. 154(b) by 962 days.

(21) Appl. No.: 12/180,085

(22) Filed: Jul. 25, 2008

(65) Prior Publication Data

US 2009/0043480 A1     Feb. 12, 2009

(30) Foreign Application Priority Data

Aug. 10, 2007 (JP) ................................. 2007-208961

(51) Int. Cl.
*A61B 17/32*     (2006.01)
(52) U.S. Cl.
USPC ........................................................ 606/167
(58) Field of Classification Search .............. 606/79, 606/83, 131, 159, 166, 167, 170; 604/27, 604/28, 35, 43, 149, 150, 289, 310, 311
See application file for complete search history.

(56) References Cited

U.S. PATENT DOCUMENTS

| | | | |
|---|---|---|---|
| 4,655,197 A | 4/1987 | Atkinson | |
| 5,643,302 A * | 7/1997 | Beiser et al. | ........... 606/167 |
| 6,322,533 B1 | 11/2001 | Gonon | |
| 6,375,635 B1 | 4/2002 | Moutafis et al. | |
| 6,423,027 B1 | 7/2002 | Gonon | |
| 6,423,028 B1 | 7/2002 | Gonon | |
| 2004/0092925 A1 | 5/2004 | Rizoiu et al. | |
| 2006/0156875 A1 | 7/2006 | McRury et al. | |

FOREIGN PATENT DOCUMENTS

| | | |
|---|---|---|
| EP | 1 199 054 A1 | 4/2002 |
| JP | A-63-99853 | 5/1988 |
| JP | A-2003-50098 | 1/2003 |
| JP | A-2005-152127 | 6/2005 |
| JP | 2006-198409 | 8/2006 |
| WO | WO 00/71038 A1 | 11/2000 |

OTHER PUBLICATIONS

Dec. 5, 2011 European Search Report issued in European Patent Application No. 08161993.4.

* cited by examiner

*Primary Examiner* — Victor Nguyen
*Assistant Examiner* — Jonathan W Miles
(74) *Attorney, Agent, or Firm* — Oliff & Berridge, PLC

(57) ABSTRACT

A fluid injection device includes a fluid supply unit that accommodates and supplies fluid, a fluid injection unit that injects fluid supplied from the fluid supply unit, and a driving waveform generating device which is equipped with at least one adjusting device, a one-input multiple-control parameter changing unit that simultaneously changes plural control parameters for determining a fluid injection condition of the fluid injection unit on the basis of a signal from the at least one adjusting device, and a driving waveform generator that generates and outputs a driving waveform of the fluid injection unit on the basis of the control parameters set by the one-input multiple-control parameter changing unit.

11 Claims, 6 Drawing Sheets

FLUID INJECTION DEVICE

BACKGROUND

1. Technical Field

The present invention relates to a fluid injection device in which the characteristic of fluid to be injected can be easily set to a desired state in accordance with various situations.

2. Related Art

With respect to a surgery based on injected fluid, the substance of an internal organ can be incised while preserving vasculature such as blood vessels, and also incidental damage applied to living tissues other than the incised site is minor. Therefore, the load imposed on a patient is small. Furthermore, bleeding is little, so that bleeding does not disturb the field of vision of an operational field and thus a rapid operation (surgery) can be performed. Therefore, this operation is frequently clinically applied particularly to hepatic resection, etc. in which bleeding from small blood vessels gives a lot of trouble (for example, JP-A-63-99853).

In the technique as disclosed in the above publication, a pump as a pressurizing source of liquid (fluid) is provided at the outside, and high-pressure fluid is led through a flexible tube to a treatment site. Therefore, even when pressure pulsation is generated by the pressurizing sourcer injection of the fluid causes continuum flow because the tube has elasticity. When the injection of fluid is pulsated flow, the incision (exsection) performance is enhanced by impact of bow wave. However, when the injection of fluid is continuum flow, the incision performance of living tissues is insufficient, and also the flow amount to be injected is large. Therefore, droplets of living tissues, etc. from the incision (exsection) site easily fly and these droplets may introduce an infection to an operator.

As an improvement proposal of the fluid injection device as described above is known a method of generating fluid jet by which means for making fluid flow is provided in a fluid chamber and vapor bubbles of fluid is intermittently generated by heating means in the fluid chamber so that the internal pressure in the fluid chamber is intermittently increased and pulsated fluid is injected at high speed (For example, JP-T-2003-500098).

Furthermore, a fluid injection device disclosed in JP-A-2005-152127 which has been filed by the inventors of this application can inject pulsated fluid at high speed and high repetitive frequency, and the control thereof is easy. Furthermore, the injection of the pulsated fluid enhances the incision performance of tissues in the operation, etc., and also makes it possible to reduce the fluid amount, so that the fluid is little trapped in the operational field. Accordingly, this method has an effect of enhancing visibility and preventing scattering of the tissues.

Only the generated pressure of the pump as the pressurizing source can be set as a control parameter in JP-A-63-99853, however, various control parameters can be set in the methods of disclosed in JP-T-2003-500098 and JP-A-2005-152127. In JP-A-2005-152127, the wave height value of pulsation, the frequency of pulsation, the pulsation number constituting a fluid stream (group), the interval between fluid streams (groups), etc. can be set as the control parameters. By setting these values properly, it is possible to properly exsect soft tissues of a living body whose hardness and structure vary every place.

For example, by increasing the wave height of pulsation, a harder tissue can be exsected. However, in the case of the same tissue, incision of the tissue concerned progresses more deeply (i.e., a deeper tissue can be also incised) by injecting the fluid for the same time. At this time, when a surgeon wants to make the exsection progress depth equal to that before the adjustment, the adjustment can be performed by reducing the pulsation number constituting the fluid stream or increasing the time interval between the fluid streams to reduce the injected fluid amount.

Furthermore, when an fluid infusion bag or the like is used to supply fluid to a fluid injection portion by using force of gravitation, the amount of fluid to be supplied is limited by the fluid resistance of a fluid channel. At this time, if the control parameters are set so that the injection amount of fluid exceeds the limit of the supplied fluid amount, the injection state of the fluid is unstable, and the exsection performance may be reduced.

However, it is very difficult that these plural control parameters which are mutually correlated with one another are properly adjusted by an surgeon or an operator under the supervision of the surgeon during a time-limited operation. Furthermore, in a fluid injection device in which the supplied fluid amount is limited by the structure thereof, even when a surgeon wants to incise a tissue more deeply and thus increase the pulsation number constituting the fluid stream, there is a case where no desired characteristic is obtained or the operation is unstable because the supplied fluid amount is limited.

SUMMARY

An advantage of the present invention is to solve at least a part of the foregoing problem, and can be implemented as the following embodiment or application example.

A fluid injection device according to an aspect of the present invention includes: a fluid supply unit that accommodates and supplies fluid; a fluid injection unit that injects fluid supplied from the fluid supply unit; and a driving waveform generating device including at least one adjusting device, a one-input multiple-control parameter changing unit that simultaneously changes plural control parameters for determining a fluid injection condition of the fluid injection unit on the basis of a signal from the at least one adjusting device and a driving waveform generator that generates and outputs a driving waveform of the fluid injection unit on the basis of the control parameters set by the one-input multiple-control parameter changing unit.

Here, the fluid injection condition means a variation state of the injection speed of a fluid stream injected from a fluid injection opening portion, and the adjusting device is an adjusting dial for selecting the hardness of a tissue as an exsection target.

According to the aspect of the present invention, an injection condition of a fluid stream (group) which a surgeon desires can be rapidly obtained. Therefore, the surgery time can be shortened, and the fatigue of the surgeon can be reduced. Furthermore, an erroneous operation of the surgeon or an operator under the supervision of the surgeon can be reduced, and a safe operation can be performed. Still furthermore, even when the amount of supplied fluid is limited, unstable settings can be prevented from being set due to deficiency of the supplied fluid amount, so that a stable operation of the fluid injection device can be implemented.

In the fluid injection device according to the aspect, it is preferable that the driving waveform is constructed by a pulsating portion and a resting portion.

For example, when the driving waveform is constructed by a pulsating portion including a waveform of an integer number of sequential sine waves starting from $-\pi/2$ in phase and a resting portion at which no waveform is output, the control parameters may be plural effective items selected from the amplitude of the sine waves, the frequency of the sine waves, the number of the sequential sine waves and the length of the resting time. In this case, the injection of the fluid stream is pulsated by the waveform of the sequential sine waves, the incision performance of a tissue is enhanced, and also the flow amount can be controlled by the resting time.

In the fluid injection device according to the aspect of the present invention, it is preferable that the one-input multiple-control parameter changing unit is equipped with a driving control parameter calculating device or an optimum control parameter setting table.

The operation of the one-input multiple-control parameter changing unit in the fluid injection device according to the aspect is determined on the basis of experiment results obtained by actually incising a model tissue or the like. Accordingly, these results are described in the optimum control parameter setting table along the experiment results rather than function approximation of the results, and the optimum control parameter setting table is referred to as occasion demands, whereby the optimum driving waveform can be simply constructed.

Furthermore, on the basis of the signal selected and input by the adjusting device, the proper control parameters can be calculated by the driving control parameter calculating device to generate and output the optimum driving waveform.

In the fluid injection device according to the aspect of the present invention, it is preferable that a plurality of optimum control parameter setting tables are provided, and the driving waveform generating device is further equipped with an adjusting device that selects one of the plural optimum control parameter setting tables.

The plural optimum control parameter setting tables are set in accordance with a surgery site as a surgery target. In such a case, the optimum control parameter setting table is selected on the basis of the surgery site as the surgery target and the initial setting based on the hardness of the surgery site, and fluid is injected on the basis of the driving waveform based on the selected optimum control parameter setting table, whereby the fluid injection device can be properly adjusted under various conditions.

In the fluid injection device according to the aspect of the present invention, it is preferable that the optimum control parameter setting table is a time-series driving waveform indicating value within a fixed time range.

The pulsating portion of the driving waveform is not limited to the sine wave described above. Accordingly, by providing the driving waveform including the pulsating portion and the resting portion on the basis of the driving waveform indicating value, a more proper fluid injection condition can be set in accordance with the hardness of the surgery site or the exsection depth.

In the fluid injection device according to the aspect of the present invention, it is preferable that the driving waveform generating device is further equipped with an adjusting device that sets the optimum gain of the generated driving waveform.

With this construction, only the gain of the driving waveform (that is, corresponding to the amplification factor of the voltage of the output pulsating portion) can be changed by using the adjusting device before or during the surgery. Accordingly, only the gain can be adjusted in accordance with the hardness of the surgery site or the exsection depth of the surgery site with changing neither the frequency nor the number of sequential driving waves, and thus the surgeon can perform his/her desired surgery.

In the fluid injection device according to the aspect of the present invention, it is preferable that the fluid injection unit has an operation environment detecting element therein, and the driving waveform generating device is equipped with a gain adjusting circuit that sets the optimum gain of the driving waveform on the basis of a detection signal from the operation environment detecting element.

Here, the operation environment detecting element is typified by a pressure sensor for fluid supplied to the fluid injection device, for example.

In the above construction, the pressure of the fluid supplied to the fluid injection unit is detected by the pressure sensor, and the pressure detection value is taken into the gain adjusting circuit to adjust the gain of the driving waveform. Accordingly, the surgeon is not required to perform the adjusting operation and only the gain can be adjusted in accordance with the hardness and surgery depth of the surgery site without affecting the frequency and the number of the sequential driving waves.

In the fluid injection device according to the aspect of the present invention, it is preferable that the driving waveform generating device is equipped with a pressure generator that supplies fluid to the fluid injection unit under an indicated pressure.

With the above construction, even when the surgeon wishes to set such a condition that it is preferable to increase the amount of fluid to be injected, the fluid is supplied under proper pressure of the pressure generator, so that the fluid stream can be stably injected.

BRIEF DESCRIPTION OF THE DRAWINGS

The invention will be described with reference to the accompanying drawings, wherein like numbers reference like elements.

DESCRIPTION OF EXEMPLARY EMBODIMENTS

Exemplary embodiments according to the present invention will be described with reference to the accompanying drawings.

Figure 3:
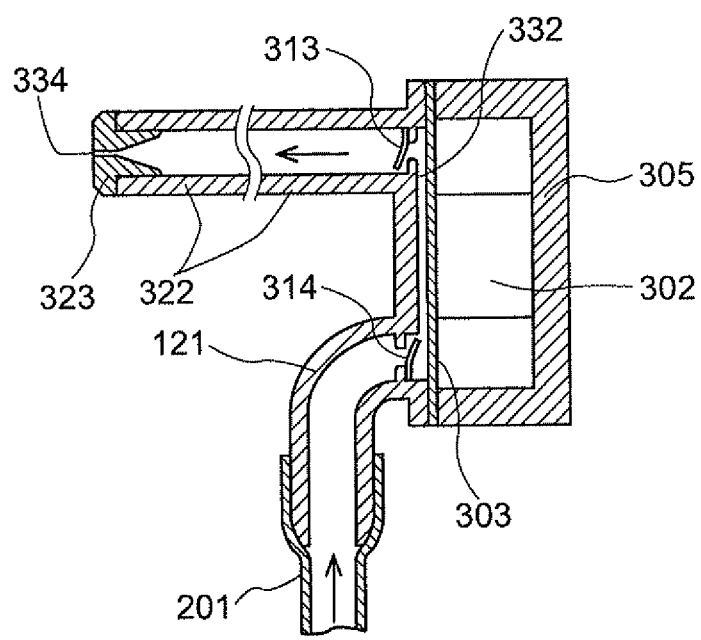
FIG. 3 is a longitudinally sectional view of a fluid injection unit according to the first embodiment.
Figure 4:
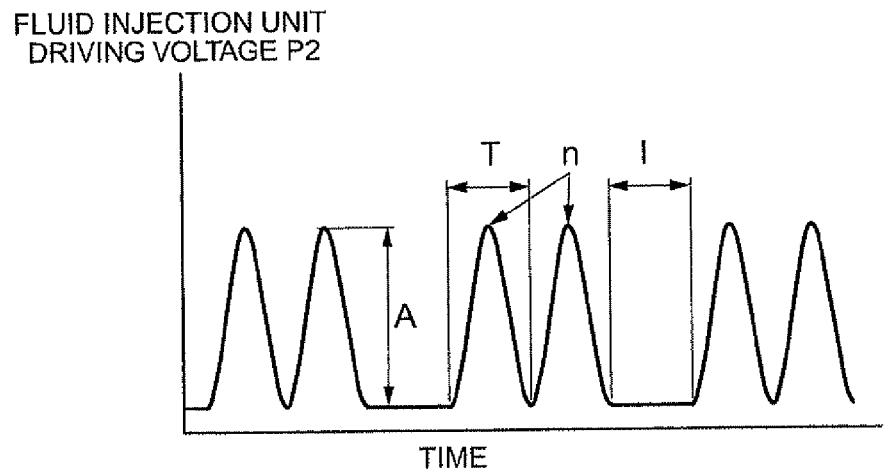
FIG. 4 is a graph showing an example of a driving voltage waveform of the fluid injection unit according to the first embodiment.
Figure 5:
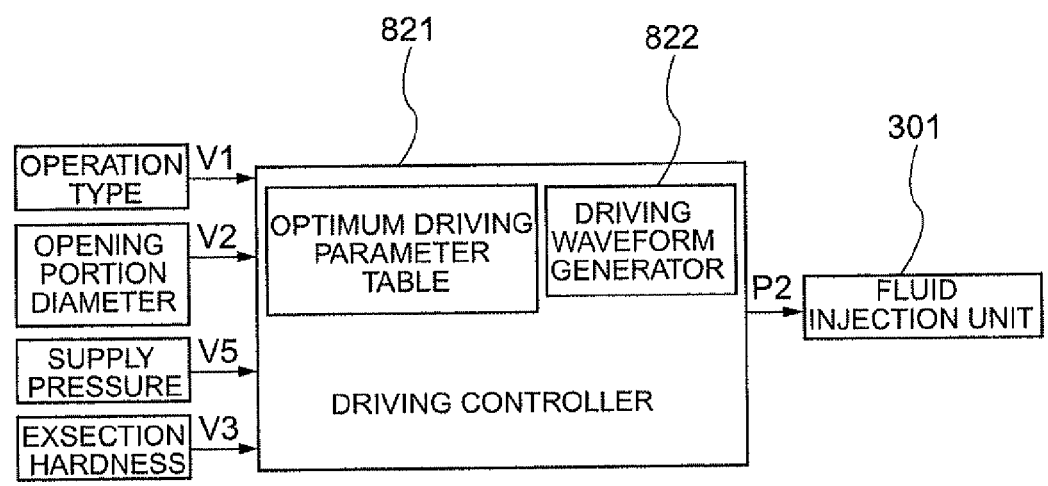
FIG. 5 is a block diagram showing the internal construction of a driving waveform generating device according to a second embodiment.
Figure 6:
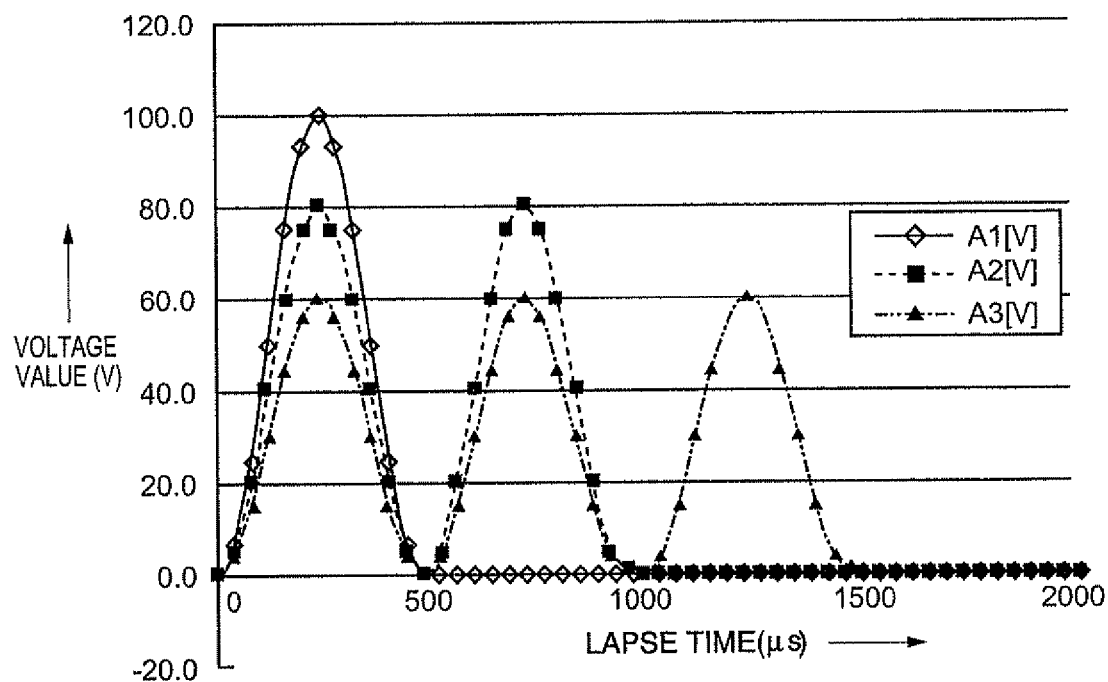
FIG. 6 shows a driving waveform formed by an optimum driving control parameter table under low supply pressure according to a third embodiment.
Figure 7:
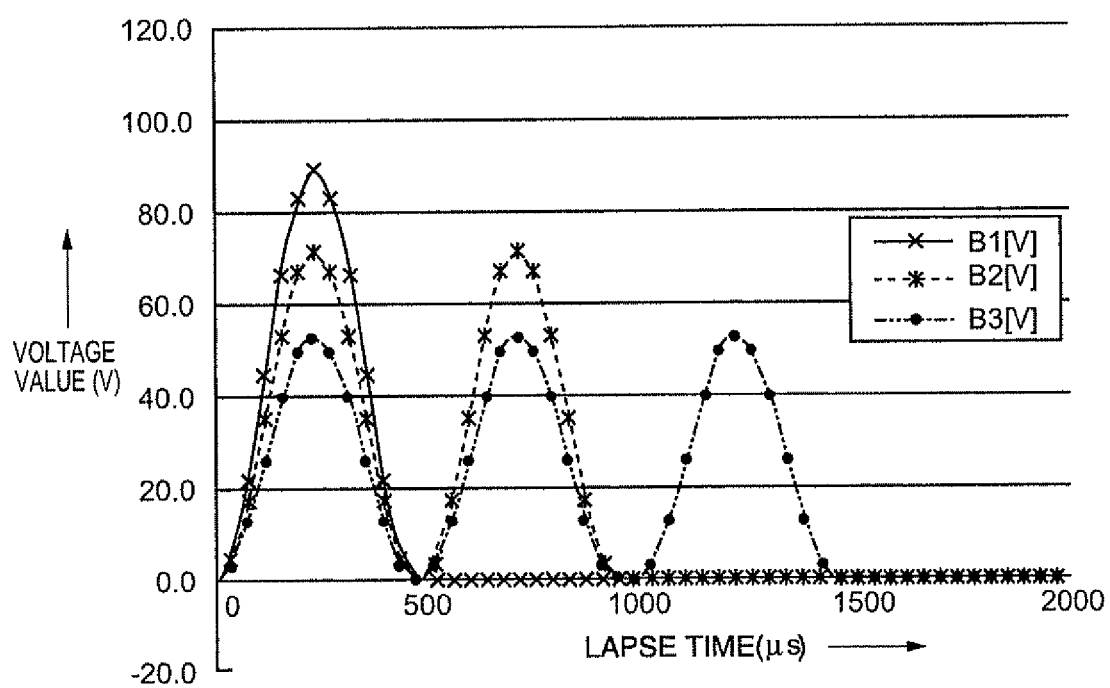
FIG. 7 shows a driving waveform formed by the optimum driving control parameter table under high supply pressure according to the third embodiment.
Figure 8:
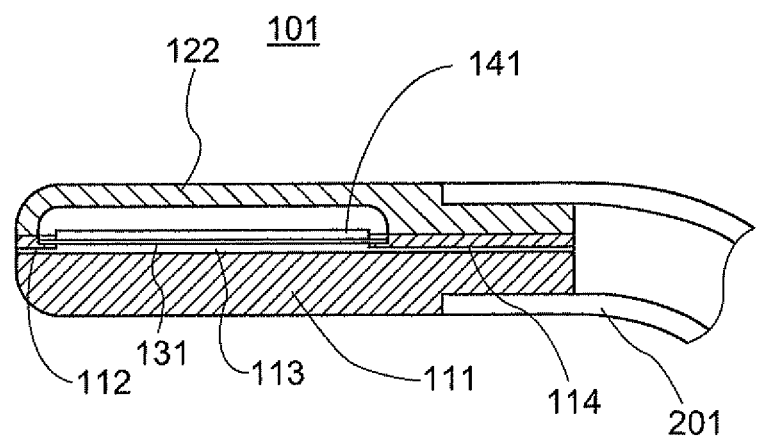
FIG. 8 is a longitudinally sectional view of a fluid injection unit according to a fourth embodiment.
Figure 9:
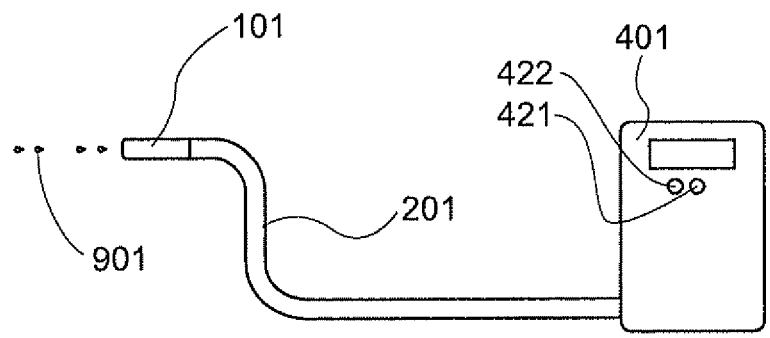
FIG. 9 is a diagram showing the schematic construction of a fluid injection device according to the fourth embodiment.

FIGS. 1 to 4 show a fluid injection unit of a fluid injection device according to a first embodiment, FIG. 5 shows a second embodiment, FIGS. 6 and 7 show a third embodiment, and FIGS. 8 and 9 show a fourth embodiment. In the drawings referred to in the following description, the horizontal-vertical scales of members and portions are different from the actual scales for convenience of illustration. Furthermore, the fluid injection device according to an embodiment of the present invention can be applied to various fields such as drawing using ink or the like, cleaning of minute objects and structures, surgical scalpel blade, etc. In the embodiments described below, the invention will be described by exemplifying a fluid injection device suitably used to incise or cut out a living body tissue, or a fluid injection device suitably combined with a catheter which is inserted in a blood vessel to remove blood clots or the like. Accordingly, fluid used in these embodiments is water, normal saline solution or the like.

First Embodiment

Figure 1:
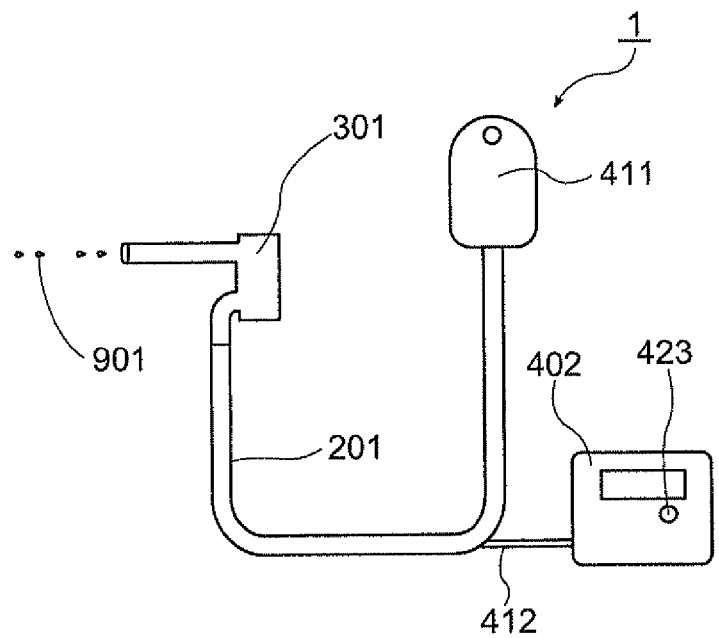
FIG. 1 is a diagram showing the schematic construction of a fluid injection device according to a first embodiment.

FIG. 1 is a diagram showing the schematic construction of a fluid injection device according to a first embodiment. In FIG. 1, the fluid injection device 1 includes, as a basic construction, a fluid infusion bag 411 serving as a fluid supply unit that accommodates fluid therein and supplies the fluid by the action of gravitational force, a fluid injection unit 301 that varies fluid supplied by the gravitational force to pulsation, and a driving waveform generating device 402.

The fluid infusion bag 411 and the fluid injection unit 301 are connected to each other through a flexible connection tube 201. The driving waveform generating device 402 and the fluid injection unit 301 are partially electrically connected to each other by a connection cable 412 disposed along the connection tube 201. The driving waveform generating device 402 is equipped with an exsection hardness adjusting dial 423 as a kind of adjusting device and a driving controller 821 (see FIG. 2).

Figure 2:
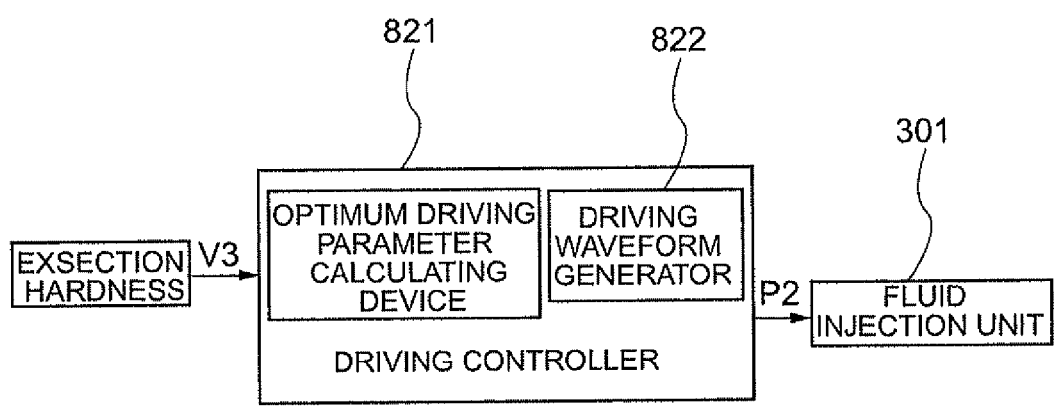
FIG. 2 is a block diagram showing the inside of a driving waveform generating device according to the first embodiment.

FIG. 2 is a block diagram showing the internal construction of the driving waveform generating device according to this embodiment. An exsection hardness indicating value V3 indicated by the exsection hardness adjusting dial 423 is input to the driving controller 821. Furthermore, a driving control parameter calculating device as a one-input multiple-control parameter changing unit is provided in the driving controller 821. Control parameters optimal to the exsection hardness indicating value V3 are calculated and a fluid injection unit driving voltage P2 corresponding to a target surgery site is output to the fluid injection unit 301 by a driving waveform generator 822. This operation will be described in more detail. The one-input multiple-control parameter changing unit means a device that can simultaneously change at least two or more control parameters by one input.

FIG. 3 is a longitudinally sectional view of the fluid injection unit. In FIG. 3, a fluid chamber 332 to which fluid is supplied from the connection tube 201 through an inlet pipe 121 is equipped with an inlet valve 314 at the entrance thereof and an outlet valve 313 at the exit thereof. The volume of the fluid chamber 332 varies by sagging of a diaphragm 303. The fluid injection unit driving voltage P2 is applied to a piezoelectric element 302, whereby the piezoelectric element 302 expands and contracts and thus the diaphragm 303 sags. One end of the piezoelectric element 302 is fixed to the bottom portion of a lid member 305, and the peripheral edge of the lid member 305 is fixed to the peripheral edge portion of the diaphragm 303. Accordingly, the diaphragm 303 sags by the expansion and contraction of the piezoelectric element 302.

When the piezoelectric element 302 contracts, the volume of the fluid chamber 332 increases, so that the outlet valve 313 is closed and the inlet valve 314 is opened. As a result, the fluid supplied from the connection tube 201 is sucked into the fluid chamber 332. When the piezoelectric element 302 expands, the volume of the fluid chamber 332 is reduced, so that the inlet valve 314 is closed and the outlet valve 313 is opened. As a result, fluid is discharged from the fluid chamber 332 to a connection fluid channel pipe 322.

The fluid discharged to the connection fluid channel pipe 322 makes a high-pressure portion under high pressure at the base portion of the connection fluid channel pipe 322. This high-pressure portion moves at the velocity of sound, and a fluid stream 901 under pulsation state is injected from a fluid injection opening portion 334 formed at a tip member 323. In order to minimize the attenuation of the pressure in the connection fluid channel pipe 322, it is necessary to minimize the deformation of the pipe line and the compression amount of fluid by pressure. Accordingly, the connection fluid channel pipe 322 is formed of a material having sufficient rigidity, and also the internal volume thereof is set to a requisite minimum value.

According to the above construction, the volume of the fluid chamber 332 can be freely increased/reduced by expanding/contracting the piezoelectric element 302. Therefore, various control parameters can be optimally controlled, and also the control frequency can be set to 10 KHz or more. Accordingly, even when the pulsation itself or the interval between pulses is long, the surgeon can perform continuous exsection with the same feeling as a continuous stream. Furthermore, there is no rise in the temperature of the injected fluid, and thus the operation (i.e., surgery) can be performed with safety.

Next, the one-input multi-control parameter change by the driving control parameter calculating device will be described with reference to FIG. 4 showing an example of the driving waveform. The fluid injection unit driving voltage P2 in the example of FIG. 4 has a pulsating portion including a waveform of an integer number of sequential sine waves starting from $-\pi/2$ in phase and a resting portion (represented by a resting time I). The waveform of the pulsating portion is represented by the amplitude A, the period T and the number n of sequential sine waves. The waveform of the pulsating portion is a burst wave, and it can be simply generated by indicating the above control parameters through the driving wave generator 822.

With respect to the exsection of a tissue by injecting pulsating fluid, as the intensity of the pulsation is large, a large tissue can be exsected. This can be implemented by increasing the amplitude A of the fluid injection unit driving voltage in FIG. 4. In this case, however, the amount of fluid to be injected per unit time is increased. As a result, the exsection depth per unit time is also increased. When the surgeon does not want increase of the exsection depth per unit time, it is necessary to reduce the number n of sequential sine waves to a proper value or increase the resting time I simultaneously with increase of the amplitude A.

In this embodiment, when the exsection hardness adjusting dial 423 is operated, the amplitude A of the fluid injection unit driving voltage as one of the control parameters increases, and at the same time the resting time I as another control parameter is varied by the driving control parameter calculating device so that the exsection depth is not varied.

This operation makes it possible to reduce the load imposed on the surgeon or the operator under supervision of the surgeon and the risk of the erroneous operation. Furthermore, when fluid is supplied by gravitational force as in the case of this embodiment and the supply amount of fluid the increase/decrease of which can not be adjusted is limited, the variation of the amount of fluid to be injected is consequently suppressed. Accordingly, there is an effect that the operation of the fluid injection device 1 is stable. When the driving control parameter calculating device is not used, the exsection hardness adjusting dial 423 may be constructed by a twin switch or a twin variable resistor.

In the above embodiment, it is preferable that the driving wave generator 822 is further equipped with an adjusting device (not shown) for setting the optimum gain of the generated driving waveform. The adjusting device may include a rotary switch, a slide switch, a variable volume or the like which is provided separately from the exsection hardness adjusting dial 423. The optimum gain of the driving waveform, that is, the peak voltage of the output driving waveform is stepwise adjusted by the rotary switch, the slide switch or the like. When the variable volume is adopted, the peak voltage can be continuously adjusted.

Accordingly, only the gain of the driving waveform can be changed by using the adjusting device before surgery or during surgery, and only the gain can be adjusted in accordance with the hardness or exsection depth of the surgery site with changing neither the frequency nor the number of sequential driving waves, whereby the surgeon can perform his/her desired surgery.

It is preferable that the fluid injection unit 301 is provided with a pressure sensor (not shown) as an operation environment detecting element, the driving waveform generating device 402 is provided with a gain adjusting circuit (not shown) and the optimum gain of the driving waveform is set on the basis of the detection signal from the pressure sensor.

With the above construction, the pressure of the fluid supplied from the fluid infusion bag 411 to the fluid injection unit 301 is detected by the pressure sensor, the pressure detection value is taken into the driving waveform generating device 402 and the optimum gain of the driving waveform is adjusted by the gain adjusting circuit. Accordingly, only the gain can be adjusted in accordance with the hardness and the surgery depth of the surgery site in connection with the fluid supply pressure without surgeon's adjusting operation of the optimum gain and without affecting the frequency and the number of sequential driving waves.

Second Embodiment

A fluid injection device according to a second embodiment will be described with reference to FIG. 5 which is a block diagram showing the internal construction of the driving waveform generating device. The second embodiment is equipped with plural optimum driving control parameter tables in place of the driving control parameter calculating device of the first embodiment.

When the fluid injection device 1 of this embodiment is used for an operation or the like, the optimum diameter of the fluid injection opening portion 334 (see FIG. 3) and the optimum range of the pulsation state of the fluid stream to be injected vary in accordance with the operation site. Therefore, it is preferable that these values are set before the operation is started and plural control parameters concerning generation of pulsation are changed within the optimum range during the operation.

In FIG. 5, V1 represents a surgery type input, V2 represents a diameter input value of the fluid injection opening portion 334, and these values are set as initial set values. The initial set values may be transmitted from a storage unit such as a memory or the like in the fluid injection unit 301 to the driving waveform generating device 402 by selecting the fluid injection unit 301 having the fluid injection opening portion 334 suitable for some operation and connecting it to the driving waveform generating device 402. In this case, input of an operator is not required, so that the operation can be simplified and the erroneous operation can be prevented.

Tables 1 and 2 shows examples of different optimum driving control parameter tables selected on the basis of initial setting values. The optimum driving control parameter tables shown in the tables 1 and 2 are selected by a rotary switch or slide switch (not shown) which is one type of adjusting device. It is preferable that these switches are protected by a cover or the like so that they are not erroneously operated during surgery.

In the tables 1 and 2, the hardness corresponds to the value represented on the exsection hardness adjusting dial 423, the voltage corresponds to the amplitude A of the fluid injection unit driving voltage represented in FIG. 4, and the space corresponds to a value obtained when the resting time I is represented by a multiple number of the period T of the sine waves constituting the pulsation. In the example of FIG. 4, the number n of the sequential sine waves is fixed to 2.

TABLE 1

| HARDNESS | VOLTAGE | SPACE |
| --- | --- | --- |
| 1 | 65 | 4 |
| 2 | 75 | 5 |
| 3 | 85 | 6 |

TABLE 2

| HARDNESS | VOLTAGE | SPACE |
| --- | --- | --- |
| 1 | 55 | 5 |
| 2 | 60 | 6 |
| 3 | 65 | 7 |

The table represented in Table 1 or 2 is selected as the initial set value by the rotary switch or the slide switch, and the hardness (exsection hardness V3) is selected by the exsection hardness adjusting dial 423. As compared with Table 1, the amplitude A of the fluid injection unit driving voltage is smaller with respect to the same value of the exsection hardness (hardness number) of the exsection hardness adjusting dial 423 and the space is larger in Table 2. Therefore, Table 2 is the optimum driving control parameter table which can be adjusted so as to be suitable for a surgery containing a surgery site containing many portions having relatively small hardness. The exsection hardness number is indicated from this optimum driving control parameter table, and the driving waveform of the fluid injection unit driving voltage P2 is output on the basis of the optimum driving control parameters to the fluid injection unit 301 by the driving waveform generator 822.

The optimum fluid injection states which are respectively suitable for different surgery sites can be easily set by selecting the optimum driving control parameter table in the manner described above. Furthermore, an erroneous exsection hardness adjusting dial value is prevented from being set during surgery, and thus there is no risk that fluid having an excessively high exsection hardness is injected, so that the operation can be safely and easily performed.

In this embodiment, a pressure sensor as an operation environment detecting element (not shown) is provided in the channel of the fluid injecting unit 301. A supply pressure signal V5 as an output signal of the operation environment detecting element for measuring the supply pressure to the fluid injection unit 301 is input to the driving controller 821. When the fluid is supplied to the fluid injection unit 301 by the fluid infusion bag 411, the state of the pulsation to be injected may vary in accordance with the difference in height between the liquid level of the fluid infusion bag 411 and the fluid injection unit 301. Therefore, the voltage (amplitude A) set in the optimum driving control parameter table is slightly corrected in accordance with the supply pressure, thereby further stabilizing the injection of the fluid.

Third Embodiment

Next, the fluid injection device according to a third embodiment will be described with reference to the drawings. The third embodiment is characterized in that the optimum driving control parameter table corresponds to time-series driving waveform indication values within a fixed time range. The construction of the fluid injection device is the same as the first embodiment, and thus the description thereof is omitted.

TABLE 3

| TIME | LOW SUPPLY PRESSURE | | | HIGH SUPPLY PRESSURE | | |
|---|---|---|---|---|---|---|
| [μsec] | A1 [V] | A2 [V] | A3 [V] | B1 [V] | B2 [V] | B3 [V] |
| 0 | 0.0 | 0.0 | 0.0 | 0.0 | 0.0 | 0.0 |
| 40 | 6.7 | 5.4 | 4.0 | 6.0 | 4.8 | 3.6 |
| 80 | 25.0 | 20.0 | 15.0 | 22.5 | 18.0 | 13.5 |
| 120 | 50.0 | 40.0 | 30.0 | 45.0 | 36.0 | 27.0 |
| 160 | 75.0 | 60.0 | 45.0 | 67.5 | 54.0 | 40.5 |
| 200 | 93.3 | 74.6 | 56.0 | 84.0 | 67.2 | 50.4 |
| 240 | 100.0 | 80.0 | 60.0 | 90.0 | 72.0 | 54.0 |
| 280 | 93.3 | 74.6 | 56.0 | 84.0 | 67.2 | 50.4 |
| 320 | 75.0 | 60.0 | 45.0 | 67.5 | 54.0 | 40.5 |
| 360 | 50.0 | 40.0 | 30.0 | 45.0 | 36.0 | 27.0 |
| 400 | 25.0 | 20.0 | 15.0 | 22.5 | 18.0 | 13.5 |
| 440 | 6.7 | 5.4 | 4.0 | 6.0 | 4.8 | 3.6 |
| 480 | 0.0 | 0.0 | 0.0 | 0.0 | 0.0 | 0.0 |
| 520 | 0.0 | 5.4 | 4.0 | 0.0 | 4.8 | 3.6 |
| 560 | 0.0 | 20.0 | 15.0 | 0.0 | 18.0 | 13.5 |
| 600 | 0.0 | 40.0 | 30.0 | 0.0 | 36.0 | 27.0 |
| 640 | 0.0 | 60.0 | 45.0 | 0.0 | 54.0 | 40.5 |
| 680 | 0.0 | 74.6 | 56.0 | 0.0 | 67.2 | 50.4 |
| 720 | 0.0 | 80.0 | 60.0 | 0.0 | 72.0 | 54.0 |
| 760 | 0.0 | 74.6 | 56.0 | 0.0 | 67.2 | 50.4 |
| 800 | 0.0 | 60.0 | 45.0 | 0.0 | 54.0 | 40.5 |
| 840 | 0.0 | 40.0 | 30.0 | 0.0 | 36.0 | 27.0 |
| 880 | 0.0 | 20.0 | 15.0 | 0.0 | 18.0 | 13.5 |
| 920 | 0.0 | 5.4 | 4.0 | 0.0 | 4.8 | 3.6 |
| 960 | 0.0 | 1.2 | 0.9 | 0.0 | 1.1 | 0.8 |
| 1000 | 0.0 | 0.0 | 0.0 | 0.0 | 0.0 | 0.0 |
| 1040 | 0.0 | 0.0 | 4.0 | 0.0 | 0.0 | 3.6 |
| 1080 | 0.0 | 0.0 | 15.0 | 0.0 | 0.0 | 13.5 |
| 1120 | 0.0 | 0.0 | 30.0 | 0.0 | 0.0 | 27.0 |
| 1160 | 0.0 | 0.0 | 45.0 | 0.0 | 0.0 | 40.5 |
| 1200 | 0.0 | 0.0 | 56.0 | 0.0 | 0.0 | 50.4 |
| 1240 | 0.0 | 0.0 | 60.0 | 0.0 | 0.0 | 54.0 |
| 1280 | 0.0 | 0.0 | 56.0 | 0.0 | 0.0 | 50.4 |
| 1320 | 0.0 | 0.0 | 45.0 | 0.0 | 0.0 | 40.5 |
| 1360 | 0.0 | 0.0 | 30.0 | 0.0 | 0.0 | 27.0 |
| 1400 | 0.0 | 0.0 | 15.0 | 0.0 | 0.0 | 13.5 |
| 1440 | 0.0 | 0.0 | 4.0 | 0.0 | 0.0 | 3.6 |
| 1480 | 0.0 | 0.0 | 0.9 | 0.0 | 0.0 | 0.8 |
| 1520 | 0.0 | 0.0 | 0.0 | 0.0 | 0.0 | 0.0 |
| 1560 | 0.0 | 0.0 | 0.0 | 0.0 | 0.0 | 0.0 |
| 1600 | 0.0 | 0.0 | 0.0 | 0.0 | 0.0 | 0.0 |
| 1640 | 0.0 | 0.0 | 0.0 | 0.0 | 0.0 | 0.0 |
| 1680 | 0.0 | 0.0 | 0.0 | 0.0 | 0.0 | 0.0 |
| 1720 | 0.0 | 0.0 | 0.0 | 0.0 | 0.0 | 0.0 |
| 1760 | 0.0 | 0.0 | 0.0 | 0.0 | 0.0 | 0.0 |
| 1800 | 0.0 | 0.0 | 0.0 | 0.0 | 0.0 | 0.0 |
| 1840 | 0.0 | 0.0 | 0.0 | 0.0 | 0.0 | 0.0 |
| 1880 | 0.0 | 0.0 | 0.0 | 0.0 | 0.0 | 0.0 |
| 1920 | 0.0 | 0.0 | 0.0 | 0.0 | 0.0 | 0.0 |
| 1960 | 0.0 | 0.0 | 0.0 | 0.0 | 0.0 | 0.0 |
| 2000 | 0.0 | 0.0 | 0.0 | 0.0 | 0.0 | 0.0 |

Table 3 shows an example or the optimum driving control parameter table according to the third embodiment. Here, the low supply pressure and the high supply pressure respectively correspond to the optimum driving control parameter tables represented in tables 1 and 2 as the initial set values, and are parameters selected in accordance with the condition of the surgery site. The selection of the low supply pressure and the high supply pressure is performed by the rotary switch or the slide switch (not shown) as one adjusting device. These switches are protected by a cover or the like so that they are not erroneously operated during the operation. A1-A3 and B1-B3 represent lapse-time-based voltage values (V) of a driving waveform which are selected by the adjusting device (for example, the exsection hardness adjusting dial 423) in accordance with the exsection hardness of the operation site. The ordinate axis represents the lapse time. That is, the optimum driving control parameter table of Table 3 represents time-series driving waveform indication values within a fixed time range.

FIGS. 6 and 7 show examples of the driving waveform formed on the basis of the optimum driving control parameter table represented in Table 3 under the low supply voltage and under the high supply voltage, respectively. The abscissa axis represents the lapse time (micro second, μS), and the ordinate axis represents the voltage value (V). Here, the driving waveform shown in FIG. 6 will be described by using A1 as a representative. The driving waveform of A1 has a pulsating portion having such a waveform that the voltage thereof gradually increases from the start time, reaches a peak voltage of 100V when 240 μs elapses, gradually decreases from the peak voltage and then reaches 0V at the lapse time of 480 μs. 0V is continued in the range from 480 μs to 2000 μs, and this area corresponds to the resting portion (resting period) I. After 2000 μs elapses, the voltage increases again. This cycle is repeated during the time period when the operation is carried out.

Likewise, A2 represents a driving waveform having a pulsating portion of two sequential driving waveforms each of which has a peak voltage of 80V, and a resting time (0V) subsequent to the two sequential driving waveforms. A3 represents a driving waveform having a pulsating portion of three sequential driving waveforms each of which has a peak voltage of 60V, and a resting time subsequent to the three sequential driving waves.

In FIG. 7, the driving waveform represented in Table 3 under high supply voltage will be described by using B1 as a representative. The driving waveform of B1 has a pulsating portion having a waveform in which the voltage gradually increases from the start time, reaches a peak voltage of 90V at the lapse time of 240 μs, gradually decreases from the peak voltage and then reaches 0V at the lapse time of 480 μs. 0V is continued in the range from the lapse time of 480 μs to 2000 μs, and this area corresponds to the resting portion I (0V). After 2000 μs elapses, the voltage increases again. This cycle is repeated.

Likewise, B2 represents a driving waveform having a pulsating portion of two sequential driving waveforms each of which has a peak voltage of 72V, and a resting time (0V)

subsequent to the two sequential driving waveforms. B3 represents a driving waveform having a pulsating portion of three sequential driving waveforms each of which has a peak voltage of 54V, and a resting time (0V) subsequent to the three sequential driving waveforms.

The waveforms of the pulsating portion and the resting time I shown in FIGS. 6 and 7 are examples, and various combinations may be applied to the waveform of the pulsating portion (represented by the voltage after a fixed time elapses, the peak voltage and the period T) and the resting time I in accordance with the hardness and exsection depth of the operation site.

The formation of the driving waveform in this embodiment is implemented by reading the time-lapse-based voltage value from the optimum driving control parameter table represented in Table 3 through a reading unit contained in the driving waveform generating device 402, shaping the respective voltage values into a continuous waveform through a smoothing wave generator (not shown) and outputting the continuous waveform concerned.

Accordingly, according to this embodiment, the waveform of the pulsating portion is not limited to the sine wave, and it is determined on the basis of the driving waveform indication values of the optimum driving control parameter table, whereby a more proper fluid injection condition can be set in accordance with the hardness or depth of the operation site.

Fourth Embodiment

Figure 10:
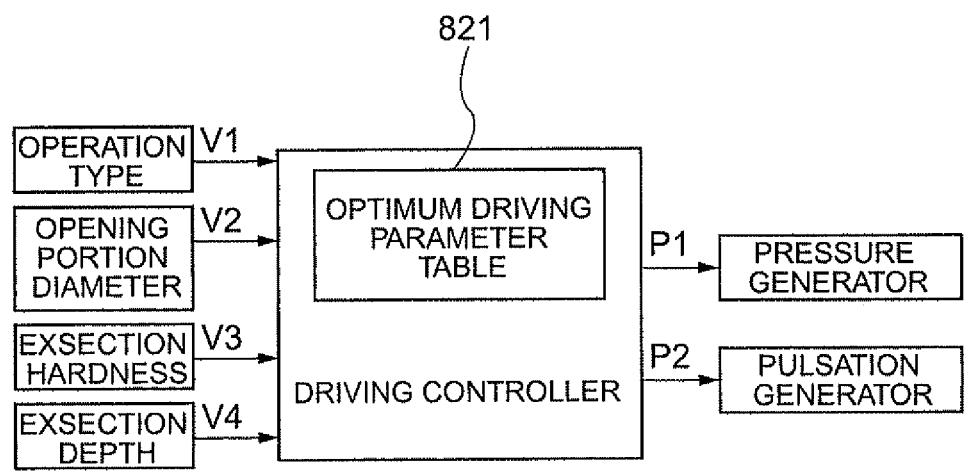
FIG. 10 is a block diagram showing the internal construction of a supply pressure control device according to the fourth embodiment.

Next, a fourth embodiment will be described with reference to FIGS. 8 to 10. According to the fourth embodiment, by combining a fluid injection unit having an outlet channel whose inertance is set to be smaller than that of an inlet channel, and a pressure generator that can generate any pressure, the range of the pulsation which can be injected can be enlarged to make the fluid injection device adaptable to various operation conditions.

The structure of the fluid injection unit according to the fourth embodiment will be first described. FIG. 8 is a longitudinal sectional view of the fluid injection unit. In FIG. 8, a recess portion forming a fluid chamber 113 is formed in the channel forming member 111. An inlet channel 114 is formed in the side wall of the fluid chamber 113, and an outlet channel 112 is formed in the side wall at the opposite side. The tip of the outlet channel 112 serves as a fluid injection opening portion.

One surface of the fluid chamber 113 is sealed by a diaphragm 131. The diaphragm 131 is provided with a piezoelectric element 141 in advance. In the piezoelectric element 141, the diaphragm 131 is set as one electrode, and an electrode member (not shown) is formed on the other confronting surface thereof and set as an counter pole electrode. Wires from these electrodes are disposed along the connection tube 201 (not shown). A cover member 122 is fixed to the channel forming member 111 so as to keep a sufficient gap so that the operation of the diaphragm 131 and the piezoelectric element 141 is not disturbed.

The maximum outer diameter of the fluid injection unit 101 is set to 3 mm or less, preferably to 2 mm or less when the fluid injection device is applied to an operation on the brain which requires exsection of minute portions, etc. Furthermore, when it is applied to a catheter or the like, the maximum outer diameter is set to 2 mm or less, preferably to 1 mm or less. The length of the fluid injection unit 101 is required to be set to 20 mm or less, preferably to 10 mm or less so that it can be freely bent. Therefore, the diaphragm 131 and the piezoelectric element 141 are minute, and the area of the diaphragm 131 which contributes to the change of the volume of the fluid chamber 113 is roughly equal to 20 $mm^2$ or less, generally to 10 $mm^2$ or less. The displacement amount thereof is generally equal to 100 μm or less.

Next, the summary of the fluidity of fluid in this fluid injection device will be described with reference to FIG. 8 and FIG. 9 showing the schematic construction of the fluid injection device according to this embodiment.

A fluid container and a pump serving as a pressure generator connected to the fluid container are contained in the supply pressure control device 401. The pump is connected to the connection tube 201 so as to feed out fluid to the connection tube 201. The fluid contained in the fluid container is supplied to the inlet channel 114 through the connection tube 201 under indicated pressure by the pump. Furthermore, the fluid is injected from the fluid injection opening portion through the fluid chamber 113 and the outlet channel 112. The fluid injection when the piezoelectric element 141 is not driven becomes a continuous stream, and the velocity of the stream is low.

The fluid injection of the fluid injection unit 101 of this embodiment is carried out on the basis of the difference between the inertance L1 at the inlet channel (which is also called as composite inertance L1) and the inertance L2 at the outlet channel (which is also called as composite inertance L2).

First, the inertance will be described. The inertance L is represented by $L=\rho \times h/S$ when the density of fluid is represented by $\rho$, the cross section of the channel is represented by S and the length of the channel is represented by h. When the pressure difference of the channel is represented by $\Delta P$ and the flow amount of the fluid flowing in the channel is represented by Q, the dynamic equation in the channel is transformed by using the inertance L, the relation of $\Delta P = L \times dQ/dt$ is derived. That is, the inertance L represents the degree of incidence applying to the time-variation of the flow amount. Accordingly, as the inertance L increases, the time-variation of the flow amount decreases, and as the inertance L decreases, the time-variation of the flow amount increases.

Furthermore, the composite inertance concerning the parallel connection of plural channels or the serial connection of plural channels having different shapes can be calculated by combining respective inertance values of individual channels in the same manner as the parallel connection or serial connection of inductance in an electrical circuit.

The connection tube 201 for connecting the pulsation and supply pressure control device 401 with the inlet channel has flexibility, and thus it may be deleted from the calculation of the inertance L1 of the inlet channel side. Furthermore, in this embodiment, the channel length and the cross sectional area of the inlet channel 114 and the channel length and the cross sectional area of the outlet channel 112 are set so that the inertance L1 of the inlet channel side is larger than the inertance L2 of the outlet channel side.

The operation of the fluid injection unit 101 will be described. Fluid is constantly supplied to the inlet channel 114 under indicated liquid pressure by the supply pressure control device 401. As a result, when the piezoelectric element 141 does not operate, the fluid flows out from the fluid injection opening portion by the fluid resistance of the inlet channel 114, the fluid chamber 113 and the outlet channel 112 and the liquid pressure described above. This flow-out speed of the fluid is very low, and it has no capability of incising or exsecting a living body tissue.

Here, when a driving signal is input to the piezoelectric element 141 and thus the piezoelectric element 141 rapidly contracts, the diaphragm 131 is rapidly bent in a convex shape so that the volume of the fluid chamber 113 is reduced. As a result, the pressure in the fluid chamber 113 rapidly increases and reaches several atms. if the inertance L1, L2 of the inlet channel side and the outlet channel side are sufficiently large.

This pressure is remarkably larger than the pulsation applied to the inlet channel 114 and the pressure based on the supply pressure control device 401. Therefore, the flow-in of the fluid from the inlet channel side into the fluid chamber 113 is reduced by the pressure concerned, and the flow-out of the fluid from the outlet channel 112 is increased. However, the inertance L1 of the inlet channel 114 is larger than the inertance L2 of the outlet channel 112, and thus the increase amount of the flow-out of the fluid from the outlet channel 112 is larger than the decrease amount of the flow-in of the fluid from the inlet channel side into the fluid chamber 113. As a result, injection 901 of pulsated fluid from the fluid injection opening portion through the outlet channel 112 occurs.

Furthermore, the inside of the fluid chamber 113 is set to a low-pressure or vacuum state by the mutual action between the reduction of the flow-in amount of the fluid from the inlet channel 114 and the increase of the flow-out amount of the fluid from the outlet channel 112 just after the pressure increases. As a result, the flow velocity of the fluid of the inlet channel 114 is restored to the same velocity before the operation of the piezoelectric element 141 by both the pressure of the pulsation and supply pressure control device 401 and the low-pressure or vacuum state in the fluid chamber 113 after a fixed time elapses.

If the piezoelectric element 141 contracts after the fluidity of the fluid in the inlet channel 114 is restored, high-speed pulsated fluid could be continuously injected from the fluid injection opening portion. The continuous state of this pulsated fluid injection is a fluid stream, and this fluid stream can be injected while leaving space (intermittently).

Accordingly, according to the fourth embodiment, the fluid is supplied to the inlet channel 114 under indicated pressure by the supply pressure control device 401, and the fluid is stably supplied to the fluid injection unit 101, so that a pump priming operation, etc. are not required in the initializing operation and a desired amount of fluid can be injected.

Next, the control of the piezoelectric element and the pressure generator will be described with reference to FIGS. 8 and 9 and FIG. 10 which is a block diagram showing the internal construction of the supply pressure control device 401.

An operation type input V1 and a fluid injection opening portion diameter input value V2 are input to the driving controller 821. This two kinds of signals may be indicated by a surgeon or an operator in the supply pressure control device 401, or it may be transmitted to the pulsation and supply pressure control device 401 from a storage unit such as a memory or the like which is provided in the fluid injection unit 101. With this construction, it is unnecessary for the operator to input, so that the operation can be simplified and the erroneous operation can be prevented.

The exsection hardness adjusting dial 421 and the exsection depth adjusting dial 422 which are provided to the pulsation and supply pressure control device 401 are adjusted by the surgeon or the operation under the supervision of the surgeon so as to be adaptable to an operation (surgery) condition which varies every second. The exsection hardness indication value V3 and the exsection depth indication value V4 which are indicated by the respective adjustment dials are input to the driving controller 821 in the supply pressure control device 401.

The optimum driving control parameter table is provided in the driving controller 821, and the fluid injection unit driving voltage P2 and the pressure indication value P1 are output as an optimum control parameter group associated with the injection of the pulsation of the fluid from the respective signals described above.

Table 4 shows an example of the optimum driving control parameter table. As in the case of the description on FIG. 4 of the first embodiment, in Table 4, the hardness represents the value of the exsection hardness adjusting dial 421, the depth represents the value of the exsection depth adjusting dial 422, the voltage represents the amplitude A of the fluid injection unit driving voltage, and the space is an multiple number of the period T of sine waves constituting the pulsation and represents the resting time I (see FIG. 4) between the pulsations.

As in the case of the second embodiment, the number n of sequential sine waves is fixed to 2. The supply pressure is a pressure indication value transmitted to the pressure generator, and its unit is atm. The number is provided for convenience of description.

The optimum driving control parameter table may be placed not in the driving controller 821, but in the fluid injection unit 101 by providing a storage unit at the fluid injection unit 101 side. In this case, the optimum driving control parameter table adapted to the operation type, the opening portion diameter, etc. is provided at the fluid injection unit 101 side, and the construction is very simple.

TABLE 4

| NUMBER | HARDNESS | DEPTH | VOLTAGE | SPACE | SUPPLY PRESSURE |
|---|---|---|---|---|---|
| 1 | 1 | 1 | 70 | 5 | 0.1 |
| 2 | 1 | 2 | 65 | 4 | 0.15 |
| 3 | 1 | 3 | 60 | 3 | 0.2 |
| 4 | 2 | 1 | 80 | 6 | 0.15 |
| 5 | 2 | 2 | 75 | 5 | 0.2 |
| 6 | 2 | 3 | 70 | 4 | 0.25 |
| 7 | 3 | 1 | 90 | 7 | 0.2 |
| 8 | 3 | 2 | 85 | 6 | 0.25 |
| 9 | 3 | 3 | 80 | 5 | 0.3 |

In Table 4, it is assumed that an operation (surgery) is carried out under the condition of the number 5. The values of the exsection hardness adjusting dial 421 and the exsection depth adjusting dial 422 are equal to 2. Here, when it is required to exsect a tissue having a higher hardness, the surgeon or the operator under the supervision of the surgeon changes the value of the exsection hardness adjusting dial 421 from 2 to 3. The condition at this time is set to the number 8. In this case, according to the optimum driving control parameter table, the amplitude A of the fluid injection unit driving voltage is changed from 75V to 85V. At this time, the space which is the multiple number of the period T of the sine waves constituting the pulsations and represents the resting time I between the pulsations is changed from 5 to 6 so that the exsection depth is not increased due to the increase of the amplitude of the pulsations, thereby suppressing increase of the flow amount. Accordingly, the variation of the flow amount itself is suppressed.

Likewise, in the case where the surgeon is carried out under the condition of the number 5, when the exsection depth is required to be increased in order to shorten the surgery time or the like, the exsection depth adjusting dial 422 may be changed from 2 to 3. The condition at this time is set to the number 6. In this case, according to the optimum driving control parameter table, the space is changed from 5 to 4, thereby increasing the flow amount. At the same time, the amplitude A of the fluid injection unit driving voltage is changed from 75V to 70V so that the hardness indication value of a tissue which can be exsected is not varied due to the increase of the flow amount. Furthermore, in order to meet the flow amount variation, the supply pressure is increased from 0.2 atm. to 0.25 atm.

As described above, according to the optimum driving control parameter table, plural control parameters are simultaneously changed so as to obtain the fluid injection which the surgeon intends, and thus a desired characteristic can be obtained by a simple operation. Accordingly, the operation (surgery) time can be shortened, and the erroneous operation can be prevented, thereby enhancing safety.

The pressure supplied from the supply pressure control device 401 is roughly set to 1 atm. (0.1 MPa) or less, preferably to 0.3 atm. (0.03 MPa) or less. When this fluid injection device is applied to a catheter or the like, the fluid injection unit 101 is required to be inserted along the inside of a blood vessel. Accordingly, it is preferable that the connection tube 201 is as flexible as possible. Therefore, it is preferable that the connection tube 201 is a flexible and thin tube and the pressure thereof is set to be low to the extent that fluid can be fed into the fluid injection unit 101. Therefore, the resistance values of the channels of the inlet channel 114, the fluid chamber 113 and the outlet channel 112 are required to be as small as possible.

Furthermore, the volume variation of the fluid chamber 113 is minute as described above, and in order to effectively use the minute volume variation for the fluid injection, it is necessary that the increase amount of the flow-out of the fluid from the outlet channel 112 is set to be larger than the reduction amount of the flow-in of the fluid from the inlet channel 114 side into the fluid chamber 113. Therefore, the inertance L1 of the inlet channel 114 is set to be larger than the inertance L2 of the outlet channel 112, and the ratio thereof is set to five times or more, preferably to ten times or more.

By setting the volume of the inlet channel 114 to a smaller value than the volume of the fluid chamber 113, the minute volume variation of the fluid chamber 113 can be suppressed from being lost by the compression caused by pressure increase of the fluid in the inlet channel 114 or the enlargement of the volume caused by deformation of surrounding members of the inlet channel 114, etc.

Furthermore, the length of the outlet channel 112, that is, the channel length from the fluid injection opening portion to the fluid chamber 113 is set to the maximum outer diameter of the fluid injection unit 101 or less. This is because the volume variation amount of the fluid chamber 113 varies in accordance with the maximum outer diameter of the fluid injection unit 101 as described above and thus the outlet channel 112 which has a shorter length and a smaller loss is required for the fluid injection unit 101 having a smaller maximum outer diameter.

Specifically, the length of the outlet channel 112 is roughly set to 1 mm or less, preferably to 0.5 mm or less. Accordingly, the distance between the fluid injection opening portion and the fluid chamber 113 is shorter, and the pulsation occurring in the fluid chamber 113 is transmitted to the fluid injection opening portion without being attenuated, so that the fluid can be efficiently injected by strong pulsations. Furthermore, by setting the length of the outlet channel 112 to a shorter value, the inertance L2 of the outlet channel 112 described above can be reduced, so that fluid can be more efficiently injected.

Furthermore, the cross-sectional area of the fluid injection opening portion may be set to be smaller than the cross-sectional area of the outlet channel 112. In this case, the injection speed of fluid from the fluid injection opening portion can be enhanced without increasing the flow channel resistance and inertance L2 of the outlet channel 112. Furthermore, the injection fluid is more minute, and thus precise injection can be performed in the operation on the brain or the like.

Still furthermore, the piezoelectric element 141 and the diaphragm 131 are adopted as the volume changing unit, so that the structure can be simplified and thus the miniaturization of the structure can be implemented. In addition, the maximum frequency of the volume variation of the fluid chamber 113 can be set to a high frequency ranging from 1 KHz to 10 KHz or more, and thus this is optimum to injection of high-speed pulsation streams.

Because the high frequency is possible, in the case where the pulsation state of the fluid stream is varied, even under a pulsation state based on repetitive fluid streams having a large period in which sine waves of 3000 Hz are used as basic waves, the number n of the fluid streams (groups) is equal to 10 and the space is set to 20, the period is equal to 1/100 second, and thus the surgeon can carry out an operation (surgery) without intending any pulsation as in the case of the continuous stream.

The entire disclosure of Japanese Patent Application No. 2007-208961, filed Aug. 10, 2007, is expressly incorporated by reference herein.

What is claimed is:

1. A fluid injection device comprising:
    a fluid supply unit that accommodates and supplies fluid;
    a fluid injection unit that incises tissue by injecting fluid supplied from the fluid supply unit; and
    a driving waveform generating device including
        at least one adjusting device,
        a one-input multiple-control parameter changing unit that simultaneously changes plural control parameters for determining a fluid injection condition of the fluid injection unit on the basis of a signal from the at least one adjusting device, and
        a driving waveform generator that generates and outputs a driving waveform of the fluid injection unit on the basis of an incision depth that is incised by the fluid, wherein the driving waveform generating device is equipped with a pressure generator that supplies the fluid to the fluid injection unit under an indicated pressure within a range of 0.3 atm to 1.0 atm.

2. The fluid injection device according to claim 1, wherein the driving waveform is constructed by a pulsating portion and a resting portion.

3. The fluid injection device according to claim 1, wherein the one-input multiple-control parameter changing unit is equipped with one of a driving control parameter calculating device and a set of predetermined control parameter values.

4. The fluid injection device according to claim 3, wherein the set of predetermined control parameter values is a time-series driving waveform indicating value within a fixed time range.

5. The fluid injection device according to claim 1, wherein a plurality of sets of predetermined control parameter values are provided, and the at least one adjusting device selects one of the plurality of sets of predetermined control parameter values.

6. The fluid injection device according to claim 1, wherein the at least one adjusting device sets a gain of the generated driving waveform.

7. The fluid injection device according to claim 1, wherein the fluid injection unit has an operation environment detecting element, and the driving waveform generating device is equipped with a gain adjusting circuit that sets a gain of the driving waveform on the basis of a detection signal from the operation environment detecting element.

8. The fluid injection device according to claim 1, wherein in response to a user-generated demand for a higher intensity of pulsation, the one-input multiple-control parameter, without user input, is configured to perform, simultaneously with the user-generated demand for the higher intensity of pulsation, at least one of: i) a reduction in sequential sine waves of the driving waveform, and ii) an increase in resting time between sequential sine waves of the driving waveform.

9. A fluid injection method, comprising:
supplying fluid with a fluid supply unit that accommodates fluid;
incising tissue with a fluid injection unit by injecting fluid supplied from the fluid supply; and
providing a driving waveform generating device including
at least one adjusting device,
a one-input multiple-control parameter changing unit that simultaneously changes plural control parameters for determining a fluid injection condition of the fluid injection unit on the basis of a signal from the at least one adjusting device, and
a driving waveform generator that generates and outputs a driving waveform of the fluid injection unit on the basis of an incision depth that is incised by the fluid, wherein the driving waveform generating device is equipped with a pressure generator that supplies the fluid to the fluid injection unit under an indicated pressure within a range of 0.3 atm to 1.0 atm.

10. A fluid injection device comprising:
a fluid supply unit that accommodates and supplies fluid;
a fluid injection unit that injects fluid supplied from the fluid supply unit; and
a driving waveform generating device including
at least one adjusting device,
a one-input multiple-control parameter changing unit that simultaneously changes plural control parameters for determining a fluid injection condition of the fluid injection unit on the basis of a signal from the at least one adjusting device, and
a driving waveform generator that generates and outputs a driving waveform of the fluid injection unit on the basis of the control parameters set by the one-input multiple-control parameter changing unit, wherein
the control parameters simultaneously changed by the one-input multiple-control parameter changing unit includes all of:
(i) an amplitude of the driving waveform,
(ii) a period of the driving waveform,
(iii) a number of sequential sine waves of the driving waveform, and
(iv) a resting time between sequential sine waves of the driving waveform.

11. The fluid injection device according to claim 10, wherein
the driving waveform generating device is equipped with a pressure generator that supplies the fluid to the fluid injection unit under an indicated pressure within a range of 0.3 atm to 1.0 atm.

* * * * *